United States Patent
Döring et al.

(10) Patent No.: US 12,043,855 B2
(45) Date of Patent: Jul. 23, 2024

(54) METHOD FOR PRODUCING GALACTOOLIGOSACCHARIDES

(71) Applicant: DMK Deutsches Milchkontor GmbH, Zeven (DE)

(72) Inventors: Sven-Rainer Döring, Zeven (DE); Marco Steffens, Elsdorf (DE)

(73) Assignee: DMK Deutsches Milchkontor GmbH, Zeven (DE)

( * ) Notice: Subject to any disclaimer, the term of this patent is extended or adjusted under 35 U.S.C. 154(b) by 23 days.

(21) Appl. No.: 17/834,149

(22) Filed: Jun. 7, 2022

(65) Prior Publication Data

US 2022/0411455 A1    Dec. 29, 2022

(30) Foreign Application Priority Data

Jun. 8, 2021    (EP) ..................................... 21178340

(51) Int. Cl.
*C12P 19/14* (2006.01)
*A23C 9/12* (2006.01)
(Continued)

(52) U.S. Cl.
CPC ............ *C12P 19/14* (2013.01); *A23C 21/023* (2013.01); *C08B 37/0036* (2013.01);
(Continued)

(58) Field of Classification Search
CPC ...... C12P 19/14; C12P 19/00; C08B 37/0036; C12N 9/2471; Y02A 50/30; A23C 21/023;
(Continued)

(56) References Cited

U.S. PATENT DOCUMENTS

2018/0201965 A1* 7/2018 Tomiuk ................... C12P 19/00
2020/0113200 A1* 4/2020 Tams ..................... A23C 9/1512

FOREIGN PATENT DOCUMENTS

CN        104004799 B   *  4/2016
CN        104004799 B      4/2016
(Continued)

OTHER PUBLICATIONS

Li, Z., et al. Production of non-monosaccharide and high-purity galactooligosaccharides by immobilized enzyme catalysis and fermentation with immobilized yeast cells. 2008, Process Biochemistry 43.8, pp. 896-899 (Year: 2008).*

*Primary Examiner* — Terry A McKelvey
*Assistant Examiner* — Andrew T Moehlman
(74) *Attorney, Agent, or Firm* — Dilworth & Barrese, LLP

(57) ABSTRACT

Suggested is method for producing galactooligosaccharides, comprising the following steps:
 (i) Providing an aqueous milk sugar solution;
 (ii) Sterilising the milk sugar solution;
 (iii) Performing a transgalactosilation of the milk sugars present in the sterilised milk sugar solution of step (ii) by adding at least one beta-galactosidase within its optimum temperature and pH value intervals for a period of at least 30 minutes, obtaining a reaction mixture;
 (iv) Inhibiting the enzyme mass in the reaction mixture of step (iii), and
 (v) Confectioning the reaction mixture of step (iv),
Wherein
 (a) The enzyme mass is wholly or partly inhibited by setting a pH value outside the activity optimum of the enzymes;
 (b) The reaction mixture, together with the inhibited enzyme mass, is subjected to filtration, obtaining a retentate (R1) and a permeate (P1);
(Continued)

(c) The inhibited amount of enzymes is separated as a retentate (R1) and is fed back to step (iii); and
(d) The permeate (P2) containing the galactooligosaccharides is passed on to step (v).

17 Claims, 1 Drawing Sheet

(51) Int. Cl.
| | |
|---|---|
| *A23C 21/02* | (2006.01) |
| *C08B 37/00* | (2006.01) |
| *C12N 9/38* | (2006.01) |
| *C12P 19/00* | (2006.01) |

(52) U.S. Cl.
CPC ............ *C12P 19/00* (2013.01); *A23C 9/1206* (2013.01); *C12N 9/2471* (2013.01)

(58) Field of Classification Search
CPC .......... A23C 9/1206; C12Y 302/01023; C07H 1/06; C07H 3/06
See application file for complete search history.

(56) References Cited

FOREIGN PATENT DOCUMENTS

| WO | 2008/037839 A1 | 4/2008 | |
|---|---|---|---|
| WO | WO-2008037839 A1 * | 4/2008 | ........... A23C 9/1206 |
| WO | 2015/034356 A1 | 3/2015 | |
| WO | WO-2020049016 A1 * | 3/2020 | ........... A23L 33/125 |
| WO | 2020/117548 A1 | 6/2020 | |

* cited by examiner

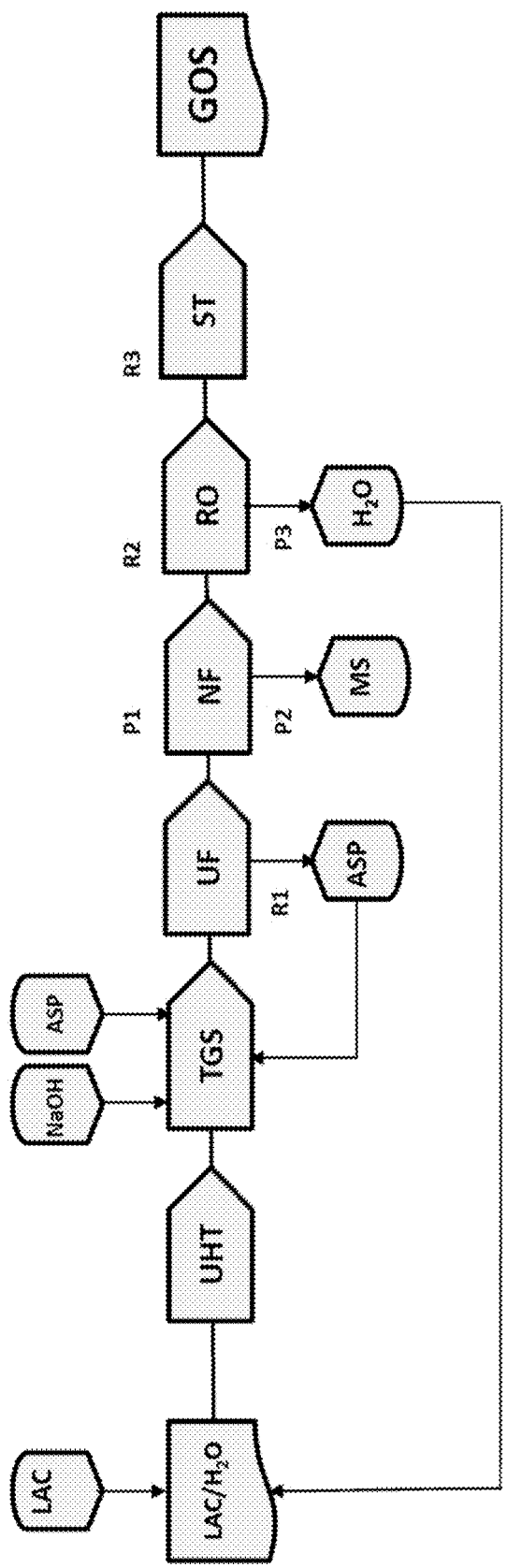

METHOD FOR PRODUCING GALACTOOLIGOSACCHARIDES

FIELD OF THE INVENTION

The present patent application relates to a method for producing specific oligomeric carbohydrates based on milk sugar.

TECHNOLOGICAL BACKGROUND

Galactooligosaccharides (GOS),

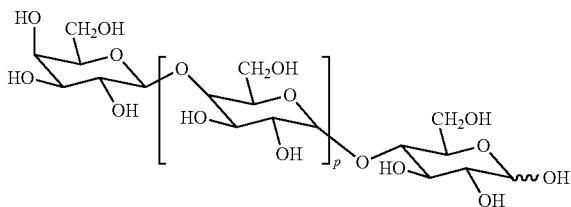

also known as oligogalactosyllactose, oligogalactose, oligolactose or transgalactooligosaccharides (TOS), belong to the group of prebiotics. GOS occur in commercially available products, such as in food for both infants and adults.

Because of the configuration of their glycosidic bonds, galactooligosaccharides (GOS) largely resist hydrolysis caused by salivary and intestinal digestive enzymes. Therefore, galactooligosaccharides are classified as prebiotics, defined as non-digestible food ingredients that beneficially affect the host by stimulating the growth and/or activity of beneficial bacteria in the colon. The increased activity of these health-promoting bacteria results in a number of effects, both directly by the bacteria themselves or indirectly by the organic acids they produce via fermentation. Examples of effects are stimulation of immune functions, absorption of essential nutrients and syntheses of certain vitamins.

Galactooligosaccharides are a substrate for bacteria, such as bifidobacteria and lactobacilli. Studies with infants and adults have shown that foods or drinks enriched with galactooligosaccharides result in a significant increase in bifidobacteria. These sugars naturally occur in human milk and are known as human milk oligosaccharides. Examples include lacto-N-tetraose, lacto-N-neotetraose and lacto-N-fucopentaose.

Human gut microbiota play a key role in the intestinal immune system. Galactooligo-saccharides support natural defences of the human body via the gut microflora, indirectly by increasing the number of bacteria in the gut and inhibiting the binding or survival of *Escherichia coli*, *Salmonella typhimurium* and *Clostridia*. GOS can positively influence the immune system indirectly through the production of antimicrobial substances, reducing the propagation of pathogenic bacteria. Constipation is a potential problem, particularly among infants, elderly, and pregnant women. In infants, formula feeding them may be associated with constipation and hard stools. GOS may improve stool frequency and relieve the symptoms related to constipation.

The typical production of GOS comprises the following steps:
1. Concentrating a milk sugar solution (lactose, acid whey, milk permeate) with the aim of reaching a dry matter of at least 30% by weight;
2. High-temperature treatment/UHT for sterilisation purposes at 85-140° C. for 90 to 300 s;
3. Adding the enzyme (e.g., *Aspergillus oryzae*) and setting the pH value and the temperature conditions that are optimal for the enzyme (e.g., pH=4.5, 55° C.);
4. The retention time is typically from more than 30 to a maximum of 120 min (depending on the enzyme), as otherwise a re-association is performed;
5. Thermal deactivation of the enzyme, for example, by high-temperature pasteurisation (90° C., 10 min);
6. Purification, optionally, concentration, spray drying.

An overview of the production of galactooligosaccharides may be found in a University Dresden online publication by K. Zerge:

RELEVANT STATE OF THE ART

EP 2620506 A1 (DUPONT) relates to the production of GOS, based on lactitol.

EP 3598901 A1 (HOCHSCHULE ANHALT) relates to a method for preparing GOS, wherein beta-galactosidase, derived from *L. bulgaricus* (*L. delbrueckii* spp. *bulgaricus*), is incubated in a lactose-containing composition, such as milk, buffer or whey, e.g., sweet whey, sour whey, whey concentrate or whey permeate, at a temperature of 37° C. or lower.

EP 3041945 B1 (FRIESLAND) provides a method for preparing GOS from lactose, comprising (i) contacting a lactose feed with immobilised beta-galactosidase (EC 3.2.1.23) and (ii) allowing for GOS synthesis, wherein said lactose feed is an aqueous slurry of crystalline lactose.

WO 2008 037839 A1 (VALIO) relates to a method for preparing milk-based GOS-containing products by treating them with a beta-galactosidase.

WO 2018 048305 A1 (UNIV GRONINGEN) describes the use of a GOS composition which comprises branched and linear GOS species having a degree of polymerisation (DP) of 3, wherein the branched DP3-GOS species are present in excess, compared with the linear DP3-GOS species, for inducing mucin glycan utilization pathways in beneficial gut bacteria in an animal.

WO 2018 210820 A1 (NOVOZYMES) claims a method in which milk substrate having a lactose content of at least 20% by weight is treated with an enzyme with transgalactosylating activity. The transgalactosylating activity of the enzyme has been increased by glycation of lysine and/or arginin residues by incubating the enzyme with high glucose concentrations at increased temperatures.

WO 2020 049016 A1 (FRIESLAND) relates to the field of hypoallergenic oligosaccharides for use in nutritional compositions, particularly oligosaccharides having prebiotic properties. Provided is a hypoallergenic composition of oligosaccharides, comprising galactooligosaccharides (GOS), wherein (i) the galactooligosaccharides (GOS) content is at least 40% by weight of the total dry matter of the composition; (ii) the allolactose content is at least 10% by weight of the total dry matter of the composition; (iii) the 6'-GL content is at least 30% by weight of the total GOS in the composition; and (iv) at least 0,5% by weight of the total GOS has a degree of polymerisation (DP) of six or above.

WO 2020 117548 A1 (DUPONT) relates to a method for providing a low lactose milk-based product having GOS fiber, in which a milk substrate having lactose is treated with a transgalactosylating enzyme to provide GOS fiber and remaining lactose; deactivating the transgalactosylating enzyme; contacting the milk-based substrate having GOS fiber with a lactase to degrade the remaining lactose to provide the low lactose milk-based product having GOS fiber, and deactivating the lactase.

WO 2020 141032 A1 (FRIESLAND) relates to the field of nutritional ingredients, in particular to economically attractive methods for producing hypoallergenic galactooligosaccharides (HA-GOS) and the use thereof in food and feed items. Provided is a method for the production of a HA-GOS preparation, comprising contacting a lactose feed with a specific betagalactosidase (EC 3.2.1.23), wherein the lactose feed is a cheese whey permeate (CWP) or a CWP that is enriched with sialyllactose (SL-CWP).

OBJECT OF THE INVENTION

Currently known processes for the production of GOS proceed both under acid and neutral conditions in a batch-wise manner, wherein the enzyme is completely lost through thermal deactivation. A preferably continuous process, at least in parts, would be desirable, wherein the enzyme can be recovered and retained for further use.

DESCRIPTION OF THE INVENTION

A first subject matter of the invention therefore relates to a method for producing galactooligosaccharides, comprising or consisting of the following steps:
(i) Providing an aqueous milk sugar solution;
(ii) Sterilising the milk sugar solution;
(iii) Performing a transgalactosilation of the milk sugars present in the sterilised milk sugar solution of step (ii) by adding at least one beta-galactosidase within its optimum temperature and pH value intervals for a period of at least 30 minutes, obtaining a reaction mixture;
(iv) Inhibiting the enzyme mass in the reaction mixture of step (iii), and
(v) Confectioning the reaction mixture of step (iv),
Wherein
(a) The enzyme mass is wholly or partly inhibited by setting a pH value outside the activity optimum of the enzymes;
(b) The reaction mixture, together with the inhibited enzyme mass, is subjected to filtration, obtaining a retentate (R1) and a permeate (P1);
(c) The inhibited amount of enzymes is separated as a retentate (R1) and is fed back to step (iii); and
(d) The permeate (P2) containing the galactooligosaccharides is passed on to step (v).

Surprisingly, it was found that rapidly changing the pH range of the reaction solution that is optimal for the enzymes acting there is an efficient, rapid and technologically simple measure to interrupt the enzymatic reaction and to inhibit the re-association of the oligomers formed. While the conventional method for deactivating the enzymes, i.e., an ultra-high temperature treatment for a few seconds, results in the killing of the enzyme material, the enzymes that have been deactivated according to the inventive method can be further used, by returning them to their optimum pH range. To this end, it is merely required to separate the enzyme mass and to feed it back into the continuous process. The separation and feeding-back processes are certainly not always 100% perfect. Therefore, it is recommended to continuously balance any enzyme loss by dosing in fresh enzyme material, so that an at least approximately constant enzyme mass is always available. Herein, "approximately" means an interval of ±5% by weight.

The combination of changing the pH value—which in the following is referred to as "pH shift"—and the separation/re-use of the enzymes employed solves the task explained above in its entirety. In particular, the economy of the method is improved, thus reducing the price of the final products, because enzymes are no longer completely lost. In addition, this method allows a continuous operation with respect to the separation and feeding back of the enzymes. Independently thereof, the method can be performed completely batch-wise in the manner described above, for example, in large fermenters.

Starting Materials

Suitable starting materials for the production of galactooligosaccharides are milk sugar solutions, such as, for example, lactose solution, acid whey or milk permeate. The suitable starting materials share a common property in that they have a sufficient amount of lactose, specifically glycosidically bound galactose.

Lactose or milk sugar is a sugar contained in milk.

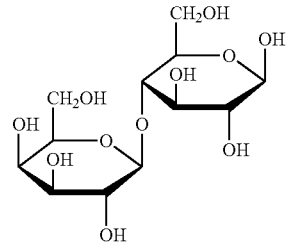

The disaccharide consists of the two molecules D-galactose and D-glucose, which form a β-1→4 glycosidic linkage. According to IUPAC, lactose is referred to as 4-O-(β-D-galactopy-ranosyl)-D-glucopyranose. It occurs as the main source of energy in mammals' milk. Lactose is digested in the small intestine by the enzyme lactase, i.e., is cleaved into glucose and galactose. Lactose forms almost the whole proportion of carbohydrates in mammals' milk and in milk products. Lactose supplies energy, supports the resorption of calcium, inhibits putrefactive bacteria in the human gut and benefits Bifidus bacteria (*Bifidobacterium*).

Whey is the aqueous greenish-yellow residual liquid obtained during the production of cheese. It is the liquid portion that may be separated after the curdling of milk in order to produce cheese or quark cheese. Acid whey is formed when milk is treated with lactic acid bacteria.

Milk permeates, particularly the ones based on skimmed milk, have been known for a long time. They are aqueous liquids obtained during filtration, in the process of which proteins and milkfat are removed from the starting material. Vitamins, mineral substances and lactose remain as residues. In principle, all known filtration methods, such as, for example, diafiltration, microfiltration, ultrafiltration, nanofiltration, reverse osmosis, electrodialysis or a combination of these steps, are suitable for obtaining milk permeates.

It is recommended to employ milk sugar solutions having a sufficiently high amount of solids (synonymous with: dry matter) in order to be able to perform the inventive method with economically reasonable conversions and yields. To do so, solutions are suitable which have a dry matter of about 25 to about 50% by weight, and preferably about 30 to about 35% by weight. Optionally, technical milk sugar solutions may be concentrated accordingly, for example, by reverse osmosis (RO).

Sterilisation

In a first step of the inventive method, the aqueous milk sugar solutions are sterilised. This is understood to be any process which allows to reduce the bacterial load of a natural starting material to a value that is below the one all national inspection authorities decided to be the threshold for approval as a food product. Typically, the milk sugar solutions are sterilised to a value of less than 1,000 germs/litre, preferably less than 500 germs/litre, and particularly about 10 to about 50 germs/litre. The preferred method of sterilisation is a high-temperature treatment in which the solutions are subjected to a temperature within the range of about 70 to about 150° C., preferably about 90 to about 120° C. for about 3 to about 300 seconds, preferably about 50 to about 200 seconds. Sterilisation can be dispensed with if a sterilised milk sugar solution is employed.

Enzymatic Transgalactosilation

In a second process step, the sterilised products are subjected to an enzymatic transgalactosilation. This is understood to be the transfer of galactose units while establishing an oligomeric sugar in the presence of suitable enzymes, in this case of beta-galactosidases, using enzymes from *Aspergillus oryzae, Bacillus circulans* or mixtures of both simultaneously or subsequently.

*Aspergillus oryzae,* more precisely *Aspergillus flavus* var. *Oryzae* is a mold (named after an aspergillum, a holy water sprinkler) that plays a significant role in Japanese cuisine. It is the most important one among the Kōji mushrooms. It is mostly used to ferment soybeans in solidstate fermentation bioreactors to produce miso and soy sauce.

*Bacillus circulans* is a species of bacteriae that spread on culture media in a circular manner, which is where its name derives from. They are anaerobically growing, gram-variable, rod-shaped, mobile cells that are 0.5 to 1 µm wide and 3.5 µm long. The bacteria ferment pentoses, hexoses, hexitols and disaccharides. *Bacillus circulans* occurs in the gut of herbivorous fish, supporting their metabolism by secreting cellulases.

As all enzymes, also beta-galactosidases unfold their optimum performance in comparably narrow temperature and pH value intervals; these are well known to the skilled person.

Therefore, with *Aspergillus oryzae,* the reaction is preferably performed at a temperature within the range of about 50 to about 60° C. and a pH value of about 4 to about 5; when adding enzymes ex *Bacillus circulans,* it is performed at a temperature within the range of about 45 to about 55° C. and a pH value of about 5.5 to about 6.5. If *Aspergillus oryzae* is employed, the method is referred to as an "acid method", in case of *Bacillus circulans,* it is referred to as a "neutral method".

One distinctive feature in the basic formation of galactooligosaccharides is that catenation is not performed continuously, but that it starts to slow down after a certain time until even the competing reaction is becoming predominant, which is the re-association of the GOS. Therefore, it has proved to be advantageous to take into account the enzyme-dependent reaction kinetics and to perform transgalactosilation for a period of about 30 to about 120 min, and particularly of about 60 to about 90 min.

pH Shift

Preferably, transgalactosilation is performed until reaching the highest concentration of GOS. This value, which is based on enzyme and reaction conditions, may be tracked by sampling; thus, a skilled person may easily determine it. When reaching the maximum of the GOS formation, the activity of the enzymes must be stopped promptly in order to avoid any re-association. Conventionally, this was achieved by a rapid high-temperature treatment in which, however, the enzyme material was completely killed. The present invention follows another path, leading the enzymes out of their optimum reaction conditions; specifically, the pH value is increased by at least two units with respect to its optimum by adding bases, or it is decreased by at least two units by adding acids. Said pH shift does not stop the reaction all of a sudden, however, it does reduce the activity of the enzymes by 80 to 90%, which is sufficient for the requirements necessary for inhibiting any noticeable re-association. To this end, it is sufficient to increase the pH to values of at least 7, preferably 8 to 12, and particularly 9 to 10, or to decrease it to values of 3 to 5, preferably 1 to 2. When adjusting the pH value it must be considered that the enzymes are not irreversibly deactivated, and that the corresponding pH value—particularly in the acid range—does not prevent any later use of the product. The pH shift may be performed by adding the required amount of usual inorganic bases, such as, for example, an aqueous NaOH, mineral acids, such as HCl, or organic acids, such as, for example, lactic acid. Increasing the pH value is preferred to decreasing it.

Separation and Re-Use of the Enzymes

The separation of the inhibited enzymes is preferably performed by filtration, particularly by ultrafiltration, which is preferably also performed continuously. The separated amount of enzymes is fed back into the reaction cycle where they directly reach the optimum ranges of temperature and pH values. Optionally, such amount of fresh enzyme may be topped up such that enzyme activity remains constant or at least approximately constant for the whole continuous process.

Confectioning: Purification, Concentration and Drying

To obtain confectionable products, the permeate of the previous step is dried and, optionally, previously purified and/or concentrated.

In a particular embodiment of the inventive method, the permeate may be subjected to nanofiltration in which undesired monosaccharides move into the permeate, enriching the amount of GOS in the retentate. Alternatively, yeasts, which digest lactose to form ethanol and carbon dioxide, may also be added to the monosaccharides. Subsequently, the yeasts may be separated, for example, in a separator or a decanter with subsequent filtration, and may be fed back into the cycle. Eventually, it is also possible to reduce the residual content of lactose by adding lactase.

To increase the concentration of GOS, the permeates may be purified, for example, by electrodialysis or by membrane methods, such as, e.g., reverse osmosis. If required, the dry matter may be increased by evaporation.

Drying, for example, is performed by lyophilisation, preferably by spray drying, in the process of which the temperature at the inlet is typically about 180 to about 260° C., and about 80 to about 105° C. at the outlet. The residual water content amounts to a maximum of 5% by weight and preferably to about 1 to about 2% by weight.

EXAMPLES

Example 1

Production of GOS According to the Neutral Method, Based on a Lactose Solution 1,000 kg of a 30% lactose solution was heated to 98° C. in a tube heat exchanger for 120 seconds, and was sterilised in the process. The sterilised solution was cooled down to 55° C., was transferred into a fermenter, was adjusted to a pH value of 4.5 by means of lactic acid, was mixed with beta-galactosidase from *Bacillus circulans* in a 1:50 weight ratio of enzyme:substrate, and was stirred. The progress of transgalactosilation was tracked by sampling. After about 90 minutes, the maximum concentration of GOS was reached. The pH value was increased to 10 within a few minutes by adding a 30% sodium hydroxide solution, as a result of which the activity of the enzyme suddenly dropped by 80%. The reaction mixture was fed to an ultrafiltration unit which was provided with a spiral wound membrane having a pore size of 10 kDa. The deactivated enzyme material was fed back to the fermenter, together with the retentate R1; to compensate any loss, 5% by weight fresh enzyme, based on the starting amount, was added. The permeate P1 was fed to a nanofiltration unit which was provided with a ceramic membrane having a pore width of 1,000 Da. The monosaccharides still contained in the product were separated together with the permeate P2, while the retentate R2 was fed to a reverse osmosis unit which was operated at a concentration factor of 1:2. The permeate P3 obtained in this process (i.e., the concentration water) was fed back into the process, the retentate R3 (i.e., the GOS concentrate) was heated to about 85° C. within the plate heat exchanger for 30 seconds and was sprayed via a tower. A white powder having a GOS content of more than 75% by weight was obtained, which still had a residual moisture of 1% by weight. The DP of the GOS was about 5% by weight.

Example 2

Production of GOS According to the Acid Method, Based on Acid Whey 1,000 kg of a ca. 30% acid whey (pH=5.1) was heated to 98° C. in a tube heat exchanger for 120 seconds, and was sterilised in the process. The sterilised solution was cooled down to 50° C., was transferred into a fermenter, was mixed with beta-galactosidase from *Aspergillus oryzae* in a 1:50 weight ratio of enzyme:substrate, and was stirred. The progress of transgalactosilation was tracked by sampling. After about 90 minutes, the maximum GOS concentration was reached. The pH value was adjusted to 10.0 within a few minutes by adding a 30% sodium hydroxide solution, as a result of which the activity of the enzyme suddenly dropped by 80%. The reaction mixture was transferred to an ultrafiltration unit which was provided with a spiral wound membrane having a pore size of 10 kDa. The deactivated enzyme material was fed back to the fermenter, together with the retentate R1; to compensate any loss, 5% by weight of fresh enzyme, based on the starting amount, was added. 0.1% by weight of the yeast *Kluyveromyces lactis* was added to the permeate P1 and was stirred at 30 to 35° C. for another 5 h. Subsequently, the suspension was fed to a second ultrafiltration unit, the yeast mass was separated as retentate R2, and was fed back, and the permeate P2 was fed to a reverse osmosis unit which was operated at a concentration factor of 1:10. The permeate P3 obtained in the process (i.e., the concentration water) was fed back into the process, the retentate R3 (i.e., the GOS concentrate) was heated to about 200° C. within the plate heat exchanger and was sprayed via a tower. A white power having a GOS content of more than 90% by weight was obtained, which still had a residual moisture of 1% by weight. The DP of the GOS was about 5% by weight.

Example 1 is further explained by means of a flowchart according to FIG. 1; herein, the abbreviations mean the following:
LAC: lactose
LAC/H2O: aqueous lactose solution
UHT: ultra-high temperature treatment
TGS: transgalactosilation
ASP: *Aspergillus oryzae*
UF: ultrafiltration
NF: nanofiltration
MS: monosaccharide
RO: reverse osmosis
ST: spray drying
GOS: galactooliogosaccharides

The invention claimed is:
1. 1. A method for producing galactooligosaccharides, comprising the following steps:
   (i) providing an aqueous milk sugar solution;
   (ii) sterilising the milk sugar solution;
   (iii) performing a transgalactosilation of the milk sugars present in the sterilised milk sugar solution of step (ii) by adding at least one beta-galactosidase within its optimum temperature and pH value intervals for a period of at least 30 minutes, obtaining a reaction mixture;
   (iv) wholly or partly inhibiting the enzyme mass in the reaction mixture of step (iii) by increasing the PH value at least two units outside the pH of optimum activity of the enzymes by adding at least one base;
   (v) performing a filtration of the reaction mixture of step (iv), together with the inhibited enzyme mass, to obtain a retentate (R1) containing an inhibited amount of the enzymesand a permeate (P1) containing the galactooligosaccharides;
   (vi) feeding the retentate (R1) back to step (iii); and
   (vii) confectioning the permeate (P1) of step (v).

2. The method of claim 1, wherein an aqueous lactose solution, acid whey, or milk permeate is employed as the milk sugar solution.

3. The method of claim 1, wherein milk sugar solutions having a dry matter of about 25 to about 50% by weight are employed.

4. The method of claim 1, wherein sterilisation is caused by high-temperature treatment.

5. The method of claim 4, wherein the high-temperature treatment is performed at a temperature within the range of about 70 to about 150° C. and for about 3 to about 300 seconds.

6. The method of claim 1, wherein enzymes from *Aspergillus oryzae* and/or *Bacillus circulans* are employed as beta-galactosidase.

7. The method of claim 6, wherein transgalactosilation is performed by adding beta-galactosidase from *Aspergillus oryzae* at a temperature within the range of about 50 to about 60° C. and a pH value of about 4 to about 5.

8. The method of claim 6, wherein transgalactosilation is performed by adding beta-galactosidase from *Bacillus circulans* at a temperature within the range of about 45 to about 55° C. and a pH value of about 5.5 to about 6.5.

9. The method of claim 1, wherein transgalactosilation is performed for a period of about 60 to about 600 min.

10. The method of claim 1, wherein the deactivated enzyme mass is separated by ultrafiltration.

11. The method of claim 1, wherein the permeate P1 is subjected to nanofiltration, the monosaccharides contained are separated as the permeate P2, and the purified retentate R2 is further processed.

12. The method of claim 1, wherein the permeate P1 is treated with a lactose digesting yeast, the yeast is separated after treatment, and the filtrate is further processed.

13. The method of claim 1, wherein the transgalactosilation product is concentrated before drying.

14. The method of claim 1, wherein the transgalactosilation product is subjected to spray drying.

15. The method of claim 1, comprising, in step (iv), increasing the pH value to at least 7.

16. The method of claim 15, comprising, in step (iv), increasing the pH value to 8-12.

17. The method of claim 16, comprising, in step (iv), increasing the pH value to 9-10.

* * * * *